(12) United States Patent
Stiene et al.

(10) Patent No.: US 6,719,923 B2
(45) Date of Patent: Apr. 13, 2004

(54) PASTE, WHICH CAN UNDERGO SCREEN PRINTING FOR PRODUCING A POROUS POLYMER MEMBRANE FOR A BIOSENSOR

(75) Inventors: Matthias Stiene, Inverness (GB); Birgit Von Tiedemann, Inverness (GB); Jamie Roders, Inverness (GB); Lucy Macgregor, Inverness (GB); Jerry McAleer, Grove (GB); Alan McNeilage, Inverness (GB)

(73) Assignee: Inverness Medical Limited (GB)

( * ) Notice: Subject to any disclaimer, the term of this patent is extended or adjusted under 35 U.S.C. 154(b) by 0 days.

(21) Appl. No.: 10/168,876

(22) PCT Filed: Oct. 18, 2001

(86) PCT No.: PCT/EP01/12073
§ 371 (c)(1),
(2), (4) Date: Nov. 4, 2002

(87) PCT Pub. No.: WO02/32559
PCT Pub. Date: Apr. 25, 2002

(65) Prior Publication Data
US 2003/0125403 A1 Jul. 3, 2003

(30) Foreign Application Priority Data
Oct. 19, 2000 (DE) .......................................... 100 52 066

(51) Int. Cl.[7] .............................. H01B 1/00; C08L 1/14; C23C 20/00

(52) U.S. Cl. .......................... 252/511; 524/39; 524/261; 524/442; 521/50; 106/1.05; 106/162.7; 106/236; 106/237; 106/241; 106/287.1; 600/309; 600/319; 600/347; 600/365; 600/395

(58) Field of Search .......................... 252/511; 524/39, 524/261, 442; 521/50; 106/1.05, 162.7, 236, 237, 241, 287.1; 600/309, 319, 347, 365, 395

(56) References Cited

U.S. PATENT DOCUMENTS

| | | | | |
|---|---|---|---|---|
| 4,425,263 A | * | 1/1984 | Nazarenko | 252/511 |
| 5,378,408 A | * | 1/1995 | Carroll et al. | 252/514 |
| 5,556,576 A | * | 9/1996 | Kim et al. | 252/511 |
| 5,607,566 A | | 3/1997 | Brown et al. | |
| 5,658,444 A | | 8/1997 | Black et al. | |
| 6,134,461 A | * | 10/2000 | Say et al. | 600/345 |

* cited by examiner

*Primary Examiner*—Samuel A. Acquah

(57) ABSTRACT

The invention relates to a paste, which can undergo screen printing, for producing a porous polymer membrane. Said paste contains at least one polymer, one or more solvents for the polymer having a boiling point of >100° C., one or more non-solvents for the polymers (pore-forming agents) having a higher boiling point than that of the solvent(s), and contains a hydrophilic viscosity modifier.

18 Claims, 6 Drawing Sheets

Figure 1:
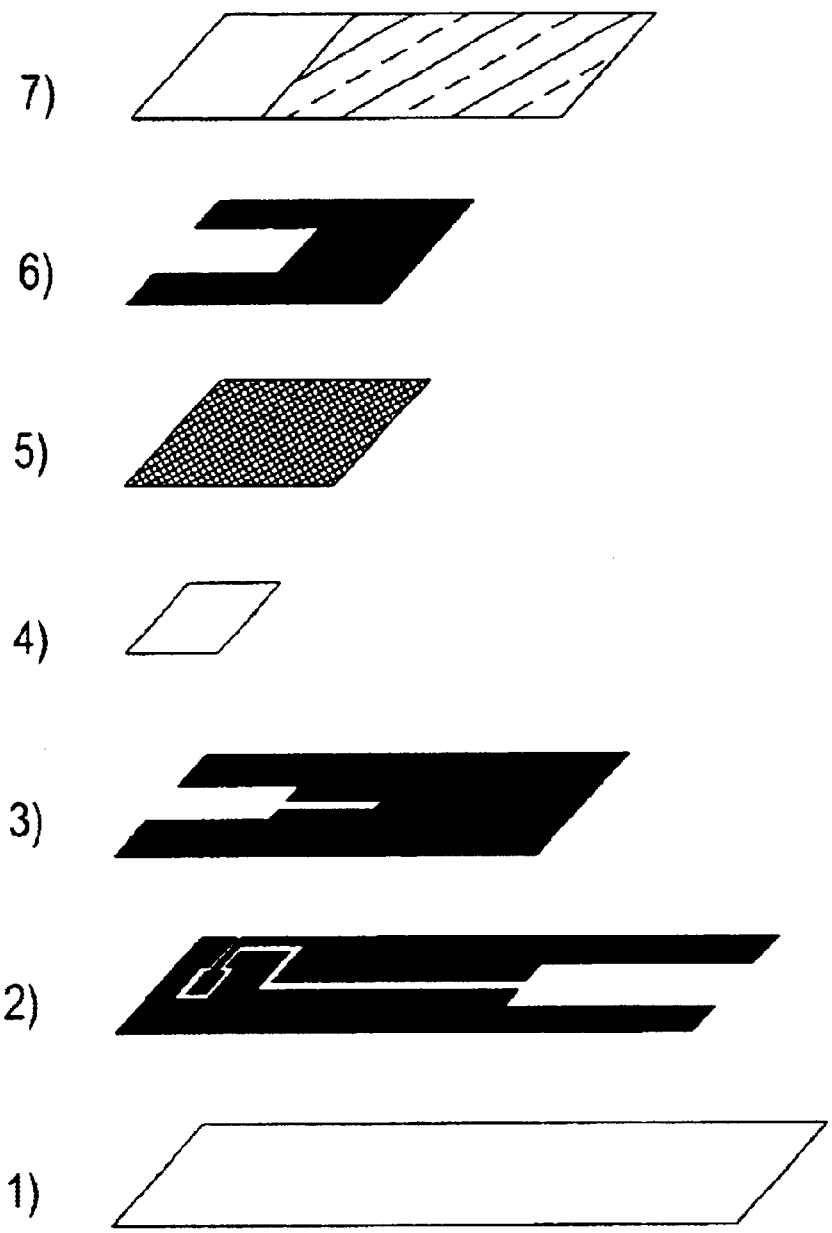

PASTE, WHICH CAN UNDERGO SCREEN PRINTING FOR PRODUCING A POROUS POLYMER MEMBRANE FOR A BIOSENSOR

The present invention relates to a screen-printable paste for producing a porous polymer membrane which can be used in electrochemical sensors, especially in electrochemical biosensors, for integrated preparation of, in particular, whole blood samples.

Biosensors are already in use in a large number of diagnostic methods, for example in the determination of the concentration of various factors in body fluids such as blood. The aim in this connection is to have sensors which require no elaborate processing of the (blood) sample but provide a rapid result simply by applying the body fluid to a test strip. This entail a specific biochemical reaction taking place, such as, for example, the enzymatic conversion of the component to be determined, which then brings about an electron transfer between different electrodes (working and reference electrodes), and this can be determined quantitatively.

The disadvantage of most or the known electrochemical biosensors is that, on application of the blood to the region provided therefor on the test strip, the biochemical reaction which takes place is influenced by other constituents present in the blood, especially the red blood corpuscles (erythrocytes). Thus, for example, when the values of the hematocrit (=volume of the erythrocytes as a proportion of the total amount of blood in vol.wt. %) are high, the value measured for glucose using conventional blood glucose sensors is lower than the actual value. This adverse affect arises from the fact that the erythrocytes influence, through adsorption onto the reactive layer of the biosensor, the diffusion of glucose into the latter and to the electrode and reduce the measured signal.

To solve this problem, various membranes which are put on top of the enzyme layer, which is disposed on the electrodes, of the test strip in order to keep the erythrocytes away from this layer have been proposed.

Thus, for example, U.S. Pat. No. 5,658,444 describes an erythrocyte exclusion membrane for a sensor, which consists of a water-insoluble, hydrophobic polymer, of a water-soluble hydrophilic polymer and of an erythrocyte aggregating agent and is produced by spraying onto the surface of the test strip.

One disadvantage of this membrane is that the membrane pore diameter varies as a function of the spraying distance and spray pressure. In addition, the spraying on of the membrane during production of the rest strip means an additional operation which is different from the production of the remainder of the test strip and is therefore elaborate, which makes the production process complicated and thus costly.

It is therefore an object of the present invention to provide a paste for producing a porous membrane which does not have the disadvantages mentioned since it can be applied during the biosensor production process by a method which fits in with the remaining procedure and is therefore cost-effective, and provides a membrane of constant pore size.

This object is achieved by a paste for a porous polymer membrane as claimed in claim 1. Advantageous developments are evident from claims 2 to 18.

The invention is explained below by means of the figures, where

Figure 2:
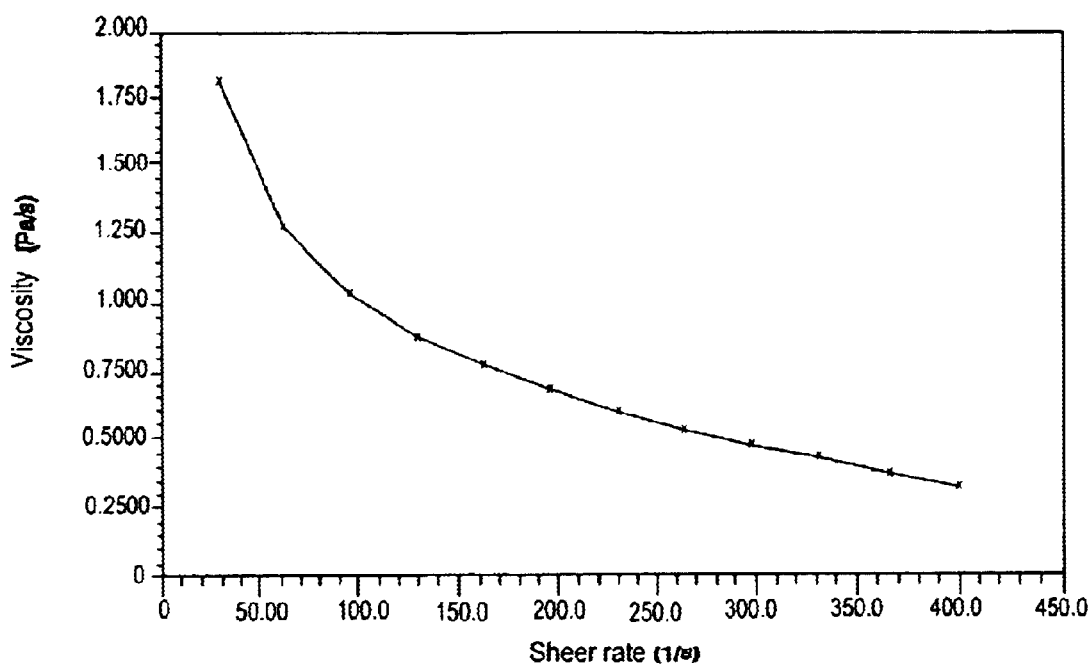
Figure 3A:
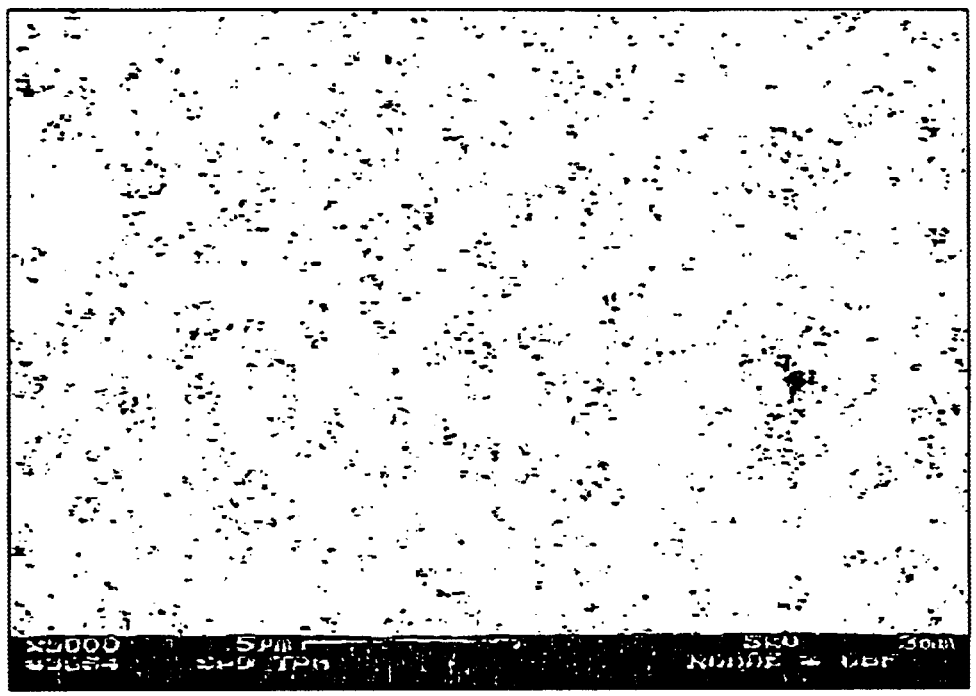
Figure 3B:
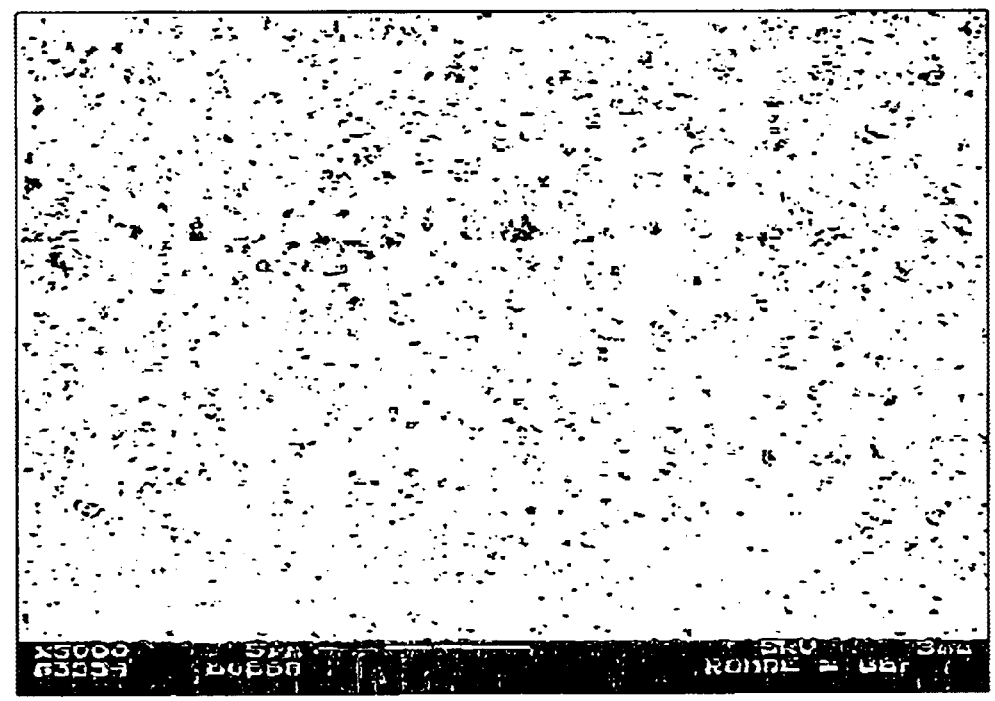
Figure 4:
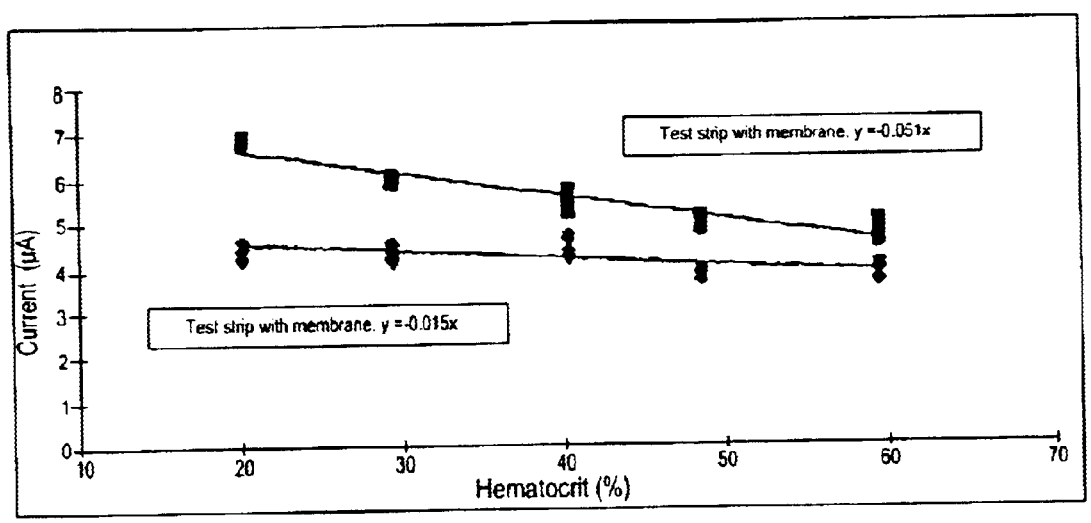
Figure 5A:
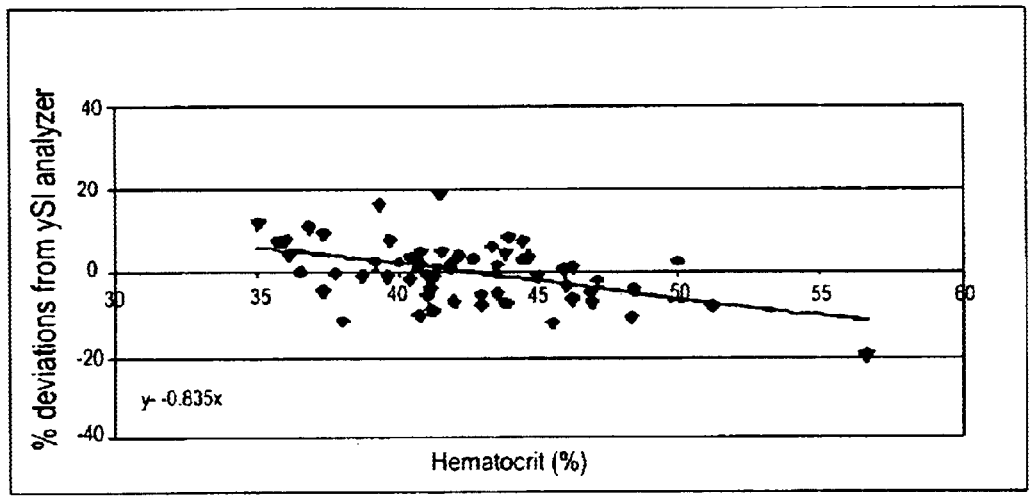
Figure 5B:
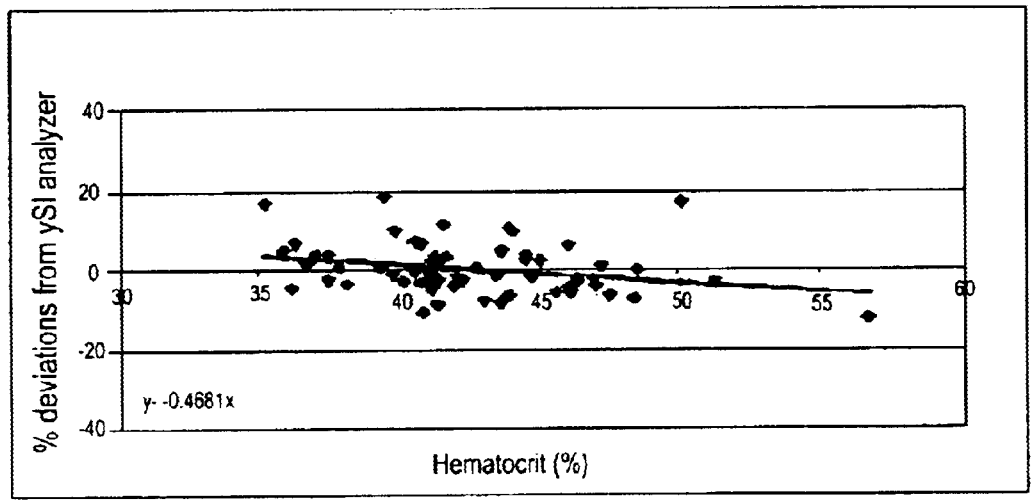
Figure 5C:
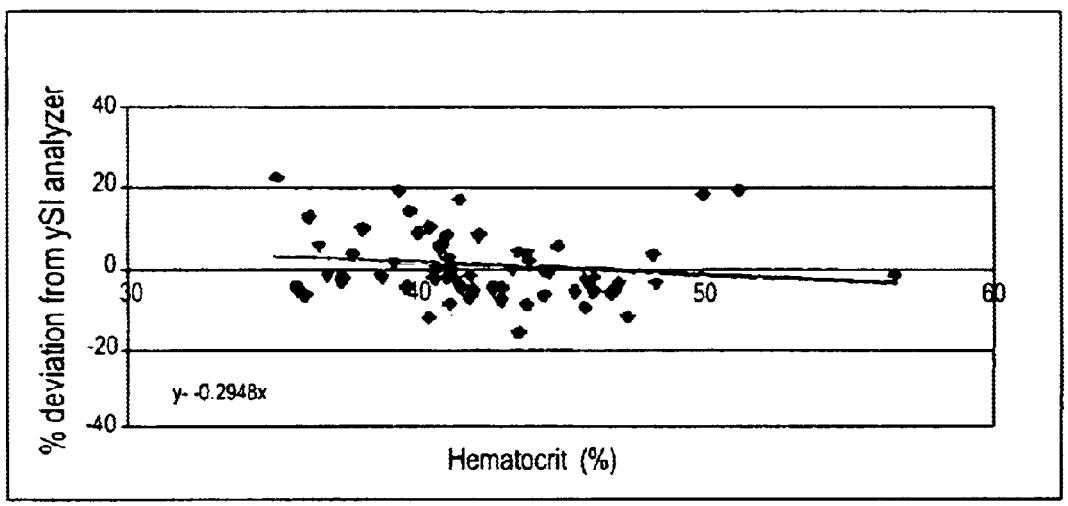
Figure 5D:
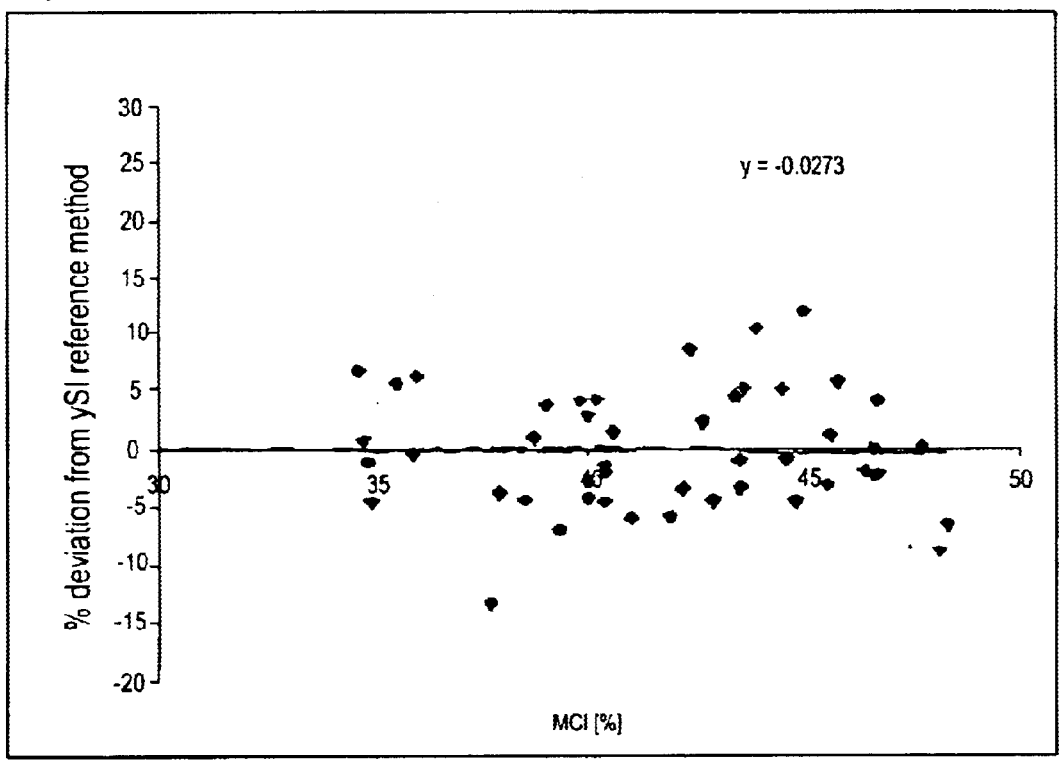

FIG. 1 shows diagrammatically the structure of a test strip with the membrane of the invention, FIG. 2 shows the theological characteristics of the paste of the invention, FIG. 3a shows an electron micrograph of a polymer membrane with inadequately developed pore structure, FIG. 3b shows an electron micrograph of the polymer membrane of the invention with well developed pore structure, FIG. 4 shows the results of measurement with two biosensors, one of them being provided with a membrane of the invention, comparing as the values of the hematocrit increase, FIGS. 5a to 5d show the clinical performance on comparison of four blood glucose sensors.

FIG. 1 depicts the structure of a test scrip with the polymer membrane of the invention. An electrode arrangement 2 in the form of a carbon layer, which in turn in partly covered by an insulation 3, is located on a polyester support material 1. An enzyme and mediator layer 4 is, disposed on the region of the electrode layer which is left free by the insulation. In the case of a blood glucose sensor, this layer comprises, for example, the enzyme glucose oxidase and the mediator $Fe^{3+}$. The polymer membrane 5 of the invention as arranged above the enzyme and mediator layer 4. The whole is covered by an adhesive layer 6 and a cover sheet 7.

In the mass production of biosensors, the screen printing method is used for printing the various layers such as electrode, insulting and enzyme layers. The present invention provides a membrane which can be applied with the same technique. On the one hand, this has the advantage that the same screen printing device can be used for printing the membrane and thus throughout the sensor production process, which involves enormous economic advantages in mass production. On the other hand, it is possible to produce by the screen printing method reproducibly a membrane of uniform thickness and pore size, which is not ensured with the other methods such as spincoating, dipping or spraying.

For it to be possible to apply the paste used to produce the polymer membrane by screen printing, the solvent(s) present therein for the polymer must have a boiling point which is as high as possible (above 100° C.) in order to avoid premature drying of the material in the printing machine. In addition, the paste comprises a nonsolvent for the polymer, which acts as pore former and has a higher boiling point than the solvent(s) used.

The paste must moreover have a suitable viscosity (30 000–50 000 cpi) in order to ensure uniform flow through the screen during the printing. The viscosity of the paste is preferably reduced on exposure to shear forces, as depicted in the rheological characteristics in FIG. 2.

The polymer preferably used in the paste of the invention is cellulose acetate (50 kDa). It is preferably present in a proportion of about 8% by weight in the screen-printable paste. In addition, a further polymer which may be present is cellulose nitrate in a proportion of up to 10% by weight.

Solvents which can be used for the polymer are, for example, 1,4-dioxane (boiling point 102° C.) and/or 4-hydroxymethylpentanone (boiling point 165° C.). A preferred composition comprise 0–20% by weight, more preferably 20% by weight, of 1,4-dioxane and 0–70% by weight, more preferably 56% by weight, of 4-hydroxymethylpentanone, it being possible alternatively to replace the 4-hydroxymethylpentanone by ethyl acetate or ethylene glycol diacetate.

It has emerged that long-chain alcohols with a boiling point of >150° C. are suitable as pore formers for the screen-printable membrane paste; preference is given to n-octanol, which hap a boiling point of 196° C., and/or 2-methyl-2,4-pentanediol (MPD), which has a boiling point of 197° C.

The paste is somewhat more tolerant to evaporation of dioxane on use of 2-metyl-2,4-pentanediol (MPD) as pore former. Moreover the cellulose acetate remains in solution longer, which extends the time during which the paste remains in a printable state. This extended "pot life" makes it possible to produce larger batches of constant quality.

The pore former should be present in a proportion of 5–20% by weight, preferably 12–15% by weight.

The viscosity modifiers used are, for example, hydrophilic silica xerogels or equivalent "fumed silicas", bentonite, clay, Natrosol or carbon black. They should be added in a proportion of from 1 to 10% by weight to the screen-printable paste. Preference is given to hydrophilic Cab-O-Sils (proprietary name for silica xerogels marketed by the Cabot organization), such as Cab-O-Sil M5, Cab-O-Sil H5, Cab-O-Sil LM50. Cab-O-Sil LM130, in a proportion of 4% by weight.

It is also possible to add further additives such as Tween 20, Triton X, Silvet 7600 or 7280, lauryl sulfate (SDS), other detergents, and polyols such as glycerol, or hydrophilic polymers such as polyvinylpyrolidone (PVP) or vinylpyrolidone/vinyl acetate copolymers (PVP/VA) to the paste of the invention.

Addition of one or more of these additives is not obligatory for producing the membrane; however it has emerged that they may improve the wetting of the membrane and speed up the sensor response. Preference is given to the use of PVP/VA or PVP in a proportion of 0.1% by weight in the screen-printable paste.

Moreover the addition of the additives Bioterge, polyethyleneimine, BSA, dextran, dicyclohexyl phthalate, gelatin, sucrose and/or biuret may improve the separation of erythrocytes and plasma.

It is additionally possible to add enzyme, for example glucose oxidase, even to the cellulose acetate paste so that printing of the enzyme layer can be dispensed with in the biosensor production process.

After application of a uniform layer of the printing paste to a suitable substrate, the membrane is formed during the drying process. There is formation of a porous layer and not of a continuous film, because the solvents used have a lower boiling point than the pore former; the solvents evaporate correspondingly quickly and the cellulose acetate polymer precipitates in the remaining film of the pore former.

However, in connection with a biosensor, it is not permissible to use just a high temperature in the drying process, because the enzymes/proteins used are denatured it the temperatures are too high. The best results were achieved in connection with a biosensor for determining glucose in whole blood with a drying temperature of about 70° C. The boiling points of the solvents and pore formers used should be selected correspondingly.

A crucial factor for the pore formation is the viscosity modifier used, which forms a gel together with the pore former in order to stabilize the polymer structure. With the substances used, the gel in produced through the interaction between the OH groups of the silica xerogel and the long-chain alcohol (e.g. octanol). The amount and the distribution of the gel produced during the drying process eventually determines the size and shape of the pores which develop.

Without addition of a viscosity modifier there is formation of an emulsion from the solvent and the pore former, because the pore former is unable on its own to stabilize the polymer skeleton. The result is a white, smooth and unstructured film with entrapped pore former, which does not allow lateral liquid transport. By comparison, a clear film is obtained when no pore former is used in the paste.

If the amounts of viscosity modifier used are too small (<1% by weight), the resulting membrane has an only inadequately developed pore structure, as shown in FIG. 3a.

Since the various suitable viscosity modifiers have different surface properties, the viscosity modifier can be selected depending on the required membrane or the required biosensor. For example, with high mechanical stress, e.g. with long printing times or on printing of very thin layers with a high squeegee pressure, the Cab-O-Sil H5 is "crushed". The surface then shows microscopically sharp fracture edges which may lead to lysis of the red blood cells.

This is an unwanted property for a blood glucose sensor because the basic current of the sensor is increased thereby. On the other hand, this effect can be optimized, and the plasma from cells be utilized directly in the sensor for the electrochemical detection. One practical example would be the examination of hemoglobin in erythrocyte. In this case, the mediator of the biosensor, e.g. potassium hexacyanoferrate (III), reacts with the Fe (II) group of the hemoglobin, producing potassium hexacyanoferrate (II) which can be determined directly at the electrode of the biosensor. An enzyme like that in the case of glucose determination is unnecessary in this came because the mediator reacts directly with the hemoglobin. It is possible in this way in practice to determine the value of the hematocrit for a patient with similar measuring equipment as in the monitoring of blood glucose, making the time-consuming use of capillary tubes and centrifuge unnecessary.

Cab-O-Sil LM 150 consists of smaller particles than H5, which are therefore more stable and are not damaged by the mechanical stress during the printing process. This viscosity modifier is therefore most suitable for producing a membrane for blood glucose sensors.

In accordance with the above statement, the difference in boiling points between solvent and pore former is, besides the stabilization of the polymer skeleton by the viscosity modifier, important for the formation of a suitable membrane. The difference should be about 30° C. in this case, so that there is formation in the drying process of a film which comprises a sufficiently high concentration of pore former in which the membrane polymer can precipitate. If the boiling point differences are smaller the pore former starts to evaporate before a critical ratio between solvent and pore former is reached, which brings about the precipitation of the membrane polymer.

After the screen-printable paste with the composition described previously has been printed, and the solvent has evaporated, there is formation through deposition of the cellulose esters of a membrane with an average pore size of from 0.1 to 2 $\mu$M, it being possible to influence the pore size by the amount of long-chain alcohol used. An electron micrograph of the membrane is shown in FIG. 3b. Since erythrocytes have an average size of 8 to 10 $\mu$m, the membrane keeps them away from the enzyme layer, while the plasma can pass through unhindered. In addition, the membrane contributes to the mechanical stability of the enzyme layer and prevents the enzyme being detached from the electrode on application of the blood sample and then no longer being available for the electrochemical reaction.

FIG. 4 illustrates by means of a series of measurements the fact that at a constant glucose concentration the test strip provided with a membrane of the invention provides, in contrast to a test strip without membrane, constant results as the values of the hematocrit increase, whereas the response with the test strip without membrane decreases as the erythrocyte concentration increases. Because of the increased diffusion barrier between the enzyme layer and the blood sample the response overall is somewhat reduced in the case of the sensor with membrane.

The invention is illustrated by means of the following examples.

Production of the Printing Paste:

In accordance with the ratios of amounts indicated in the following examples, a mixture of the solvent (e.g. hydroxymethylpenanone, dioxane) and the pore former (e.g. octanol, MPD) is produced to ensure uniform distribution of the two substances. In the next step, all the additives (e.g. PVP/VA) are added and dissolved, if necessary with the aid of ultrasound. The membrane polymer (cellulose actate 50 kDa) is then mixed rapidly with the previously produced solvent until a uniform suspension results. This suspension is rolled for 48 h in a closed container until a clear gel results, and it is possible to add the viscosity modifier (e.g. Cab-O-Sil) to this. The finished printing paste is rolled for a further 24 h in order to ensure uniform distribution of the viscosity modifier.

EXAMPLE 1

| Polymer(s): | |
|---|---|
| Cellulose acetate (Mw 30 000) | 7.5% by weight |
| Solvent: | |
| Ethylene glycol diacetate (b.p. 186° C.) | 65.5% by weight |
| Pore former: | |
| n-Decanol (b.p. 231° C.) | 25.0% by weight |
| Viscosity modifier: | |
| Cab-O-Sil M5 | 2.0% by weight |

EXAMPLE 2

| Polymer(s): | |
|---|---|
| Cellulose acetate (Mw 50 000) | 8.0% by weight |
| Solvents: | |
| 1,4-Dioxane (b.p. 102° C.) | 35.0% by weight |
| Ethyl acetate (b.p. 154° C.) | 35.0% by weight |
| Pore former: | |
| n-Octanol (b.p. 196° C.) | 18.0% by weight |
| Viscosity modifier: | |
| Cab-O-Sil M5 | 4.0% by weight |

EXAMPLE 3

| Polymer(s): | |
|---|---|
| Cellulose acetate (Mw 50 000) | 8.0% by weight |
| Solvents: | |
| 1,4-Dioxane (b.p. 102° C.) | 20.0% by weight |
| 4-Hydroxymethylpentanone (b.p. 165° C.) | 56.0% by weight |
| Pore former: | |
| n-Octanol (b.p. 196° C.) | 12.0% by weight |
| Viscosity modifier: | |
| Cab-O-Sil M5 | 4.0% by weight |
| Additives: | |
| PVP/VA | 0.1% by weight |

EXAMPLE 4

| Polymer(s): | |
|---|---|
| Cellulose acetate (Mw 50 000) | 7.4% by weight |
| Solvents: | |
| 1,4-Dioxane (b.p. 102° C.) | 18.5% by weight |
| 4-Hydroxymethylpentanone (b.p. 165° C.) | 55.6% by weight |
| Pore former: | |
| 2-Methyl-2,4-pentanediol | 14.8% by weight |
| Viscosity modifier: | |
| Cab-O-Sil M5 | 3.7% by weight |
| Additives: | |
| PVP/VA | 0.1% by weight |

FIG. 5 shows the clinical performance of blood glucose sensors
a) without polymer membrane
b) with polymer membrane (composition of Example 2)
c) with polymer membrane (composition of Example 3)
d) with polymer membrane (composition of Example 4).

In the comparative clinical investigations, the results of measurement with the various types of sensors were compared with the results of measurement by the reference method (YSI Model 2300 Stat Plus), and the percentage deviation was plotted against the values of the hematocrit for the individual blood samples. The result in the ideal case is a measurement line horizontal to the x axis. The gradient of these measurement lines, which is shown in Table 1, provides information about the interference of the hematocrit with the sensor system used.

TABLE 1

| | Gradient of the measurement lines | Gradient in % |
|---|---|---|
| Type 1 (no membrane) | −0.8253 | 100% |
| Type 2 (membrane from Example 2) | −0.4681 | 56% |
| Type 3 (membrane from Example 3) | −0.2946 | 35% |
| Type 4 (membrane from Example 4) | −0.0273 | 3.3% |

The data unambiguously reveal the superior performance of the sensor system with the preferred membrane (composition of Example 4). This improvement is achieved through the separation of whole blood and plasma directly in front of the electrode, because the Nernst diffusion layer in front of the electrode can no longer be extended into the region with erythrocytes and therefore also can no longer be influenced by different values of the hematocrit.

The following comparative examples describe printing pastes in which there is no suitable accordance between the pore former, the solvents and the viscosity modifier.

Comparative Example 1

| Polymer(s): | |
|---|---|
| Cellulose acetate (Mw 50 000) | 8.0% by weight |
| Solvent: | |
| Ethylene glycol diacetate (b.p. 186° C.) | 76.0% by weight |
| Pore former: | |
| n-Octanol (b.p. 196° C.) | 12.0% by weight |
| Viscosity modifier: | |
| Cab-O-Sil M5 (hydrophilic) | 4.0% by weight |
| Additives: | |
| PVP/VA | 0.1% by weight |

Comparative Example 2

| Polymer(s): | |
|---|---|
| Cellulose acetate (Mw 50 000) | 8.0% by weight |
| Solvents: | |
| 1,4-Dioxane (b.p. 102° C.) | 20.0% by weight |
| 4-Hydroxymethylpentanone (b.p. 165° C.) | 56.0% by weight |
| Pore former: | |
| n-Octanol (b.p 196° C.) | 12.0% by weight |
| Viscosity modifier: | |
| Cab-O-Sil TS720 (hydrophobic) | 4.0% by weight |
| Additives: | |
| PVP/VA | 0.1% by weight |

Comparative Example 3

| Polymer(s): | |
|---|---|
| Cellulose acetate propionate (Mw 75 000) | 8.0% by weight |
| Solvents: | |
| 1,4-Dioxane (b.p. 102° C.) | 20.0% by weight |
| 4-Hydroxymethylpentanone (b.p. 165° C.) | 56.0% by weight |
| Pore former: | |
| n-Octanol (b.p. 196° C.) | 12.0% by weight |
| Viscosity modifier: | |
| Cab-O-Sil M5 (hydrophilic) | 4.0% by weight |
| Additives: | |
| PVP/VA | 0.1% by weight |

In Comparative Example 1 there is no formation of a porous membrane because the difference between the boiling points of the solvent (ethylene glycol diacetate) and pore former (n-octanol) used in the printing paste is too small. If, by contrast, n-decanol is used as pore former (as described in Example 1), a porous membrane is obtained after the drying process because the boiling point between the solvent and the pore former is sufficiently large.

In Comparative Example 2 there is only inadequate gel formation between the pore former and the viscosity modifier, because of the use of hydrophobic Cab-O-Sil which is unable to react with the OH groups of the pore former, and thus there is inadequate stabilization of the polymer skeleton. This impedes the formation of a porous membrane.

No porous membrane is formed in Comparative Example 3 either, where the solubility of the polymer used (cellulose acetate propionate) in the pore is too high.

What is claimed is:

1. A screen-printable paste for producing a porous polymer membrane, comprising at least one polymer, one or more solvents for the polymer with a boiling point of >100° C., one or more nonsolvents (pore formers) for the polymer with a higher boiling point than the solvent(s) and a hydrophilic viscosity modifier.

2. A screen-printable paste as claimed in claim 1, characterized in that the difference of the boiling points of solvent and pore former is at least 30° C.

3. A screen-printable paste as claimed in claim 1, characterized in that the paste comprises cellulose acetate as polymer.

4. A screen-printable paste as claimed in claim 3, characterized in that the paste comprises 1,4-dioxane and/or 4-hydroxymethylpentanone and/or ethyl acetate as solvent.

5. A screen-printable paste as claimed in claim 4, characterized in that the paste comprise a long-chain alcohol as pore former.

6. A screen-printable paste as claimed in claim 5, characterized in that the paste comprises n-octanol and/or 2-methyl-2,4-pentanediol as pore former.

7. A screen-printable paste as claimed in claim 6, characterized in that n-octanol and/or 2-methyl-2,4-pentanediol is present in a proportion of 5–20% by weight.

8. A screen-printable paste as claimed in claim 1, characterized in that the paste comprises hydrophilic silica xerogel as viscosity modifier.

9. A screen-printable paste as claimed in claim 8, characterized in that the silica xerogel is present in a proportion of 1–10% by weight.

10. A screen-printable paste as claimed in claim 1, characterized in that the paste additionally comprises vinylpyrolidone/vinyl acetate copolymer (PVP/VA) and/or polyvinylpyrolidone (PVP).

11. A screen-printable paste as claimed in claim 10, characterized in that the PVP/VA or PVP is present in a proportion of 0.1% by weight.

12. A screen-printable paste as claimed in claim 1, characterized in that the paste additionally comprises one or more enzymes.

13. A method for producing a screen-printable paste, by
producing a mixture of one or more solvent(s) for a polymer and one or more nonsolvent(s) for a polymer (pore former),
mixing in the polymer until a uniform suspension results,
rolling the suspension until a clear gel results, adding a hydrophilic viscosity modifier, and
rolling the mixture until the viscosity modifier is uniformly distributed.

14. The use of the paste as claimed in claim 1, for producing a porous polymer membrane.

15. The use as claimed in claim 14, where the polymer membrane is introduced into a biosensor test strip.

16. The use as claimed in claim 15, characterized in that the biosensor is designed for measuring the blood glucose concentration.

17. The use as claimed in claim 15, characterized in that the biosensor is designed for determining the value of the hematocrit.

18. A porous polymer membrane produced from the screen-printable paste as claimed in claim 14.

* * * * *